US005969095A

United States Patent [19]
Dong

[11] Patent Number: 5,969,095
[45] Date of Patent: Oct. 19, 1999

[54] ANALOGS OF PARATHYROID HORMONE

[75] Inventor: Zheng Xin Dong, Framingham, Mass.

[73] Assignee: Biomeasure, Inc., Milford, Mass.

[21] Appl. No.: 08/779,768

[22] Filed: Jan. 7, 1997

Related U.S. Application Data

[63] Continuation-in-part of application No. 08/626,186, Mar. 29, 1996, Pat. No. 5,723,577
[60] Provisional application No. 60/001,105, Jul. 13, 1995, and provisional application No. 60/003,305, Sep. 6, 1995.

[51] Int. Cl.$^6$ .......................... A61K 38/29; C07K 14/635
[52] U.S. Cl. .............................................. 530/324; 514/12
[58] Field of Search .............................. 436/86; 530/324, 530/399; 514/12

[56] References Cited

U.S. PATENT DOCUMENTS

| | | | |
|---|---|---|---|
| 4,656,250 | 4/1987 | Morita et al. | 530/324 |
| 5,434,246 | 7/1995 | Fukuda et al. | 530/324 |
| 5,589,452 | 12/1996 | Krstenansky et al. | 514/12 |
| 5,599,792 | 2/1997 | Kronis et al. | 514/12 |
| 5,723,577 | 3/1998 | Dong | 530/324 |

FOREIGN PATENT DOCUMENTS

| | | |
|---|---|---|
| 0 293 158 | 11/1988 | European Pat. Off. . |
| 0 451 867 | 10/1991 | European Pat. Off. . |
| 0 561 412 | 9/1993 | European Pat. Off. . |
| 0 748 817 | 12/1996 | European Pat. Off. . |
| 2 269 176 | 2/1994 | United Kingdom . |
| WO 90 10067 | 9/1990 | WIPO . |
| WO 93 06846 | 4/1993 | WIPO . |
| WO 94/01460 | 1/1994 | WIPO . |
| WO 94/02510 | 2/1994 | WIPO . |
| WO 95/02610 | 1/1995 | WIPO . |
| WO 96/19246 | 6/1996 | WIPO . |
| WO 96 40775 | 12/1996 | WIPO . |
| WO 97 02834 | 1/1997 | WIPO . |

OTHER PUBLICATIONS

Caprole, Lynn H., et al., "Characterization of Parathyroid Hormone Antagonists", in "Peptides, Chemistry and Biology: Proceedings 10th American Peptide Symposium, St. Louis, 1987", Marshall, G.M. (Ed.), pp. 449–451 (1988).
Horiuchi, N., et al., "Similarity of Synthetic Peptide From Human Tumor To Parathyroid Hormone In Vivo and In Vitro", Science, vol. 238, pp. 1566–1568, 1987.
Gardella, T.J., et al: "Parathyroid Hormone (PTH)–PTH–Related Peptide Hybrid Peptides Reveal Functional Interactions Between The 1–14 and 15–34 Domains of the Ligand", J. Biol. Chem., vol. 270, No. 12, pp. 6584–6588, 1995.
Barden et al., "NMR Solution Structure of Human Parathyroid Hormone (1–34)", Biochemistry 32:7126–7132, 1993.
Cohen et al., "Analogues of Parathyroid Hormone Modified at Positions 3 and 6", The Journal of Biological Chemistry 266:1997–2004, 1991.
Karle et al., "Structural Characteristics of α–Helical Peptide Molecules Containing Aib Residues", Biochemistry 29:6747–6756, 1990.
Leaffer et al., "Modulation of Osteogenic Cell Ultrastructure by RS–23581, and Analog of Human Parathyroid Hormone (PTH)–Related Peptide–(1–34), and Bovine PTH–(1–34)", Endocrinology 136:3624–3631, 1995.
Li et al., "A Measure of Helical Propensity for Amino Acids in Membrane Environments", Structural Biology 1:368–373, 1994.
McLean et al., "Minimal Peptide Length for Interaction of Amphipathic α–Helical Peptides with Phosphatidylcholine Liposomes", Biochemistry 30:31–37, 1991.
Neugebauer et al., "Structural Elements of Human Parathyroid Hormone and Their Possible Relation to Biological Activities", Biochemistry 31:2056–2063, 1992.
Surewicz et al., "Structure–function Relationships in Human Parathyroid Hormone: The essential role of Amphiphilic α–Helix", Peptide Hormones 556–558.(Not dated).
Chorev, et al., "Modification of Position 12 in Parathyroid Hormone and Parathyroid Hormone Related Protein" Biochemistry, (1990) vol. 29, No. 6, pp. 1580–1586.
Strickland et al., "Structure of Human Parathyroid Hormone (1–34) in the Presence of Solvents and Micelles", Biochemistry 32;6050–6057, 1993.

*Primary Examiner*—Jeffrey E. Russel
*Attorney, Agent, or Firm*—John D. Conway; Fish & Richardson

[57] ABSTRACT

Peptide variants of fragment (1–34) of parathyroid hormone, in which at least one of the amino acid residues at positions 7, 11, 23, 24, 27, 28, and 31 is cyclohexylalanine, or at least one of the amino acid residues at positions 3, 16, 17, 18, 19, and 34 is α-aminoisobutyric acid; or, alternatively, at least the amino acid residue at position 1 is α,β-diaminopropionic acid, the amino acid residue at position 27 is homoarginine, or the amino acid residue at position 31 is norleucine.

1 Claim, No Drawings

ANALOGS OF PARATHYROID HORMONE

CROSS REFERENCE TO RELATED APPLICATIONS

This application is a continuation-in-part of U.S. application Ser. No. 08/626,186 filed Mar. 29, 1996 now U.S. Pat No. 5,723,577 which in turn claims priority from U.S. provisional application 60/001,105 filed Jul. 13, 1995 and U.S. provisional application 60/003,305 filed Sep. 6, 1995.

BACKGROUND OF THE INVENTION

Parathyroid hormone ("PTH") is a polypeptide produced by the parathyroid glands. The mature circulating form of the hormone is comprised of 84 amino acid residues. The biological action of PTH can be reproduced by a peptide $NH_2$; fragment of its N-terminus (e.g. amino acid residues 1 through 34). Parathyroid hormone-related protein ("PTHrP") is a 139 to 173 amino acid-protein with N-terminal homology to PTH. PTHrP shares many of the biological effects of PTH including binding to a common PTH/PTHrP receptor. Tregear, et al., Endocrinol., 93:1349 (1983). PTH peptides from many different sources, e.g., human, bovine, rat, chicken, have been characterized. Nissenson, et al., Receptor, 3:193 (1993).

PTH has been shown to both improve bone mass and quality. Dempster, et al., Endocrine Rev., 14:690 (1993); and Riggs, Amer. J. Med., 91 (Suppl. 5B):37S (1991). The anabolic effect of intermittently administered PTH has been observed in osteoporotic men and women either with or without concurrent antiresorptive therapy. Slovik, et al., J. Bone Miner. Res., 1:377 (1986); Reeve, et al., Br. Med. J., 301:314 (1990); and Hesch, R-D., et al., Calcif. Tissue Int'l, 44:176 (1989).

SUMMARY OF THE INVENTION

In one aspect, the invention relates to peptide variants of PTH(1–34) of the following generic formula:

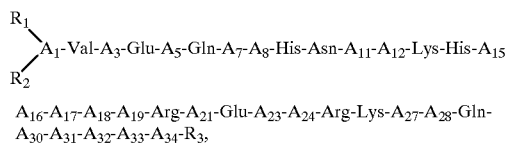

$A_{16}$-$A_{17}$-$A_{18}$-$A_{19}$-Arg-$A_{21}$-Glu-$A_{23}$-$A_{24}$-Arg-Lys-$A_{27}$-$A_{28}$-Gln-$A_{30}$-$A_{31}$-$A_{32}$-$A_{33}$-$A_{34}$-$R_3$, wherein
$A_1$ is Ser, Ala, or Dap;
$A_3$ is Ser, Thr, or Aib;
$A_5$ is Leu, Nle, Ile, Cha, β-Nal, Trp, Pal, Phe or p-X-Phe, in which X is OH, a halogen, or $CH_3$;
$A_7$ is Leu, Nle, Ile, Cha, β-Nal, Trp, Pal, Phe, or p-X-Phe in which X is OH, a halogen, or $CH_3$;
$A_8$ is Met, Nva, Leu, Val, Ile, Cha, or Nle;
$A_{11}$ is Leu, Nle, Ile, Cha, β-Nal, Trp, Pal, Phe or p-X-Phe in which X is OH, a halogen, or $CH_3$;
$A_{12}$ is Gly or Aib;
$A_{15}$ is Leu, Nle, Ile, Cha, β-Nal, Trp, Pal, Phe, or p-X-Phe in which X is OH, a halogen, or $CH_3$;
$A_{16}$ is Ser, Asn, Ala, or Aib;
$A_{17}$ is Ser, Thr, or Aib;
$A_{18}$ is Met, Nva, Leu, Val, Ile, Nle, Cha, or Aib;
$A_{19}$ is Glu or Aib;
$A_{21}$ is Val, Cha, or Met;
$A_{23}$ is Trp or Cha;
$A_{24}$ is Leu or Cha;
$A_{27}$ is Lys, Aib, Leu, hArg, Gln, or Cha;
$A_{28}$ is Leu or Cha;
$A_{30}$ is Asp or Lys;
$A_{31}$, is Val, Nle, Cha, or deleted;
$A_{32}$ is His or deleted;
$A_{33}$ is Asn or deleted;
$A_{34}$ is Phe, Tyr, Amp, Aib, or deleted;
each of $R_1$ and $R_2$ is, independently, H, $C_{1-12}$ alkyl, $C_{2-12}$ alkenyl, $C_{7-20}$ phenylalkyl, $C_{11-20}$ napthlalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkenyl, $C_{7-20}$ phenylalkyl, $C_{11-20}$ napthyalkyl, $C_{1-12}$ hydroxyalkyl, $C_{2-12}$ hydroxyalkenyl, $C_{7-20}$ hydroxy-phenylalkyl, or $C_{11-20}$ hydroxynaphthylalkyl; and
$R_3$ is OH, $NH_2$, $C_{1-12}$ alkoxy, or NH—Y—$CH_2$—Z in which Y is a $C_{1-12}$ hydrocarbon moiety and Z is H, OH, $CO_2H$, or $CONH_2$;
provided that (i) at least one of $A_5$, $A_7$, $A_8$, $A_{11}$, $A_{15}$, $A_{18}$, $A_{21}$, $A_{23}$, $A_{24}$, $A_{27}$, $A_{28}$, and $A_{31}$ is Cha, or at least one of $A_3$, $A_{12}$, $A_{16}$, $A_{17}$, $A_{18}$, $A_{19}$, and $A_{34}$ is Aib; or that (ii) at least $A_1$ is Dap, $A_7$ is β-Nal, Trp, Pal, Phe, or p-X-Phe, $A_{15}$ is β-Nal, Trp, Pal, Phe, or p-X-Phe, $A_{27}$ is hArg, or $A_{31}$ is Nle; or a pharmaceutically acceptable salt thereof.

A subset of the compounds covered by the above formula are those in which at least one of $A_5$, $A_7$, $A_{11}$, $A_{15}$, $A_{18}$, $A_{21}$, $A_{23}$, $A_{24}$, $A_{27}$, $A_{28}$, and $A_{31}$ is Cha, For example, $A_3$ is Ser; $A_5$ is Ile; $A_7$ is Leu or Cha; $A_8$ is Met, Nva, Leu, Val, Ile, or Nle; $A_{11}$ is Leu or Cha; $A_{12}$ is Gly; $A_{15}$ is Leu or Cha; $A_{16}$ is Asn or Aib; $A_{17}$ is Ser; $A_{18}$ is Met or Nle; $A_{21}$ is Val; $A_{27}$ is Lys, hArg, or Cha; $A_{32}$ is His; $A_{31}$ is Val, Nle, or Cha; $A_{33}$ is Asn; $A_{34}$ is Phe, Tyr, Amp, or Aib; $R_1$ is H; $R_2$ is H; and $R_3$ is $NH_2$; provided that at least one of $A_5$, $A_7$, $A_8$, $A_{11}$, $A_{15}$, $A_{18}$, $A_{21}$, $A_{23}$, $A_{24}$, $A_{27}$, $A_{28}$, and $A_{31}$ is Cha, or at least one of $A_3$, $A_{12}$, $A_{16}$, $A_{17}$, $A_{18}$, $A_{19}$, and $A_{34}$ is Aib. If desired, at least one of $A_7$ and $A_{11}$ can be Cha; or at least one of $A_{15}$, $A_{23}$, $A_{24}$, $A_{27}$, $A_{28}$, and $A_{31}$ is Cha.

In another subset, at least one of $A_3$, $A_{12}$, $A_{16}$, $A_{17}$, $A_{18}$, $A_{19}$, and $A_{34}$ is Aib. For example, $A_3$ is Ser or Aib; $A_5$ is Ile; $A_7$ is Leu or Cha; $A_8$ is Met, Nva, Leu, Val, Ile, or Nle; $A_{11}$ is Leu or Cha; $A_{15}$ is Leu or Cha, $A_{16}$ is Asn or Aib; $A_{18}$ is Met, Aib, or Nle; $A_{21}$ is Val; $A_{27}$ is Lys, Aib, Leu, hArg, or Cha; $A_{31}$ is Val, Nle, or Cha; $A_{32}$ is His; $A_{33}$ is Asn; $A_{34}$ is Phe, Tyr, Amp, or Aib; $R_1$ is H; $R_2$ is H; and $R_3$ is $NH_2$; provided that at least one of $A_5$, $A_7$, $A_8$, $A_{11}$, $A_{15}$, $A_{18}$, $A_{21}$, $A_{23}$, $A_{24}$, $A_{27}$, $A_{28}$, and $A_{31}$ is Cha, or at least one of $A_3$, $A_{12}$, $A_{16}$, $A_{17}$, $A_{18}$, $A_{19}$, and $A_{34}$ is Aib. If desired, at least one of $A_7$ and $A_{11}$ can be Cha; or at least one of $A_{15}$, $A_{23}$, $A_{24}$, $A_{27}$, $A_{28}$, and $A_{31}$ is Cha.

In a still further subset, at least one of $A_5$, $A_7$, $A_8$, $A_{11}$, $A_{15}$, $A_{18}$, $A_{21}$, $A_{23}$, $A_{24}$, $A_{27}$, $A_{28}$, and $A_{31}$ is Cha, or at least one of $A_3$, $A_{12}$, $A_{16}$, $A_{17}$, $A_{18}$, $A_{19}$, and $A_{34}$ is Aib. For example, $A_3$ is Ser or Aib; $A_5$ is Ile; $A_7$ is Leu or Cha; $A_8$ is Met, Nva, Leu, Val, Ile, or Nle; $A_{11}$ is Leu or Cha; $A_{15}$ is Leu or Cha; $A_{16}$ is Asn or Aib; $A_{18}$ is Met, Aib, or Nle; $A_{21}$ is Val; $A_{27}$ is Lys, Aib, Leu, hArg, or Cha; $A_{31}$ is Val, Nle, or Cha; $A_{32}$ is His; $A_{33}$ is Asn; $A_{34}$ is Phe, Tye, Amp, or Aib; $R_1$ is H; $R_2$ is H; and $R_3$ is $NH_2$. If desired, at least one of $A_7$ and $A_{11}$, is Cha and at least one of $A_{16}$, $A_{19}$, and $A_{34}$ is Aib; or at least one of $A_{24}$, $A_{28}$, and $A_{31}$ is Cha and at least one of $A_{16}$ and $A_{17}$ is Aib.

In yet another subset, at least one of $A_1$ is Dap, $A_7$ is β-Nal, Trp, Pal, Phe or p-X-Phe, $A_{13}$ is β-Nal, Trp, Pal, Phe, or p-X-Phe. For example, $A_1$ is Ser, Gly, or Dap; A3 is Ser or Aib; $A_8$ is Met, Nva, Leu, Val, Ile, or Nle; $A_{16}$ is Asn or Aib; $A_{18}$ is Met, Aib, or Nle; $A_{21}$ is Val; $A_{27}$ is Lys, Aib, Leu, hArg, or Cha; $A_{31}$ is Val, Nle, or Cha; $A_{32}$ is His; $A_{33}$ is Asn; $A_{34}$ is Phe, Tyr, Amp, or Aib; $R_1$ is H; $R_2$ is H; and $R_3$ is $NH_2$.

The following are examples of the peptide of this invention as covered by the above formula: [Cha$^7$]hPTH (1–34) NH$_2$; [Cha$^{11}$]hPTH(1–34)NH$_2$; [Cha$^{15}$]hPTH (1–34)NH$_2$; [Cha$^{7, 11}$]hPTH(1–34)NH$_2$; [Cha$^{7, 11}$, Nle$^{8, 18}$, Tyr$^{34}$]hPTH (1–34)NH$_2$; [Cha$^{23}$]hPTH(1–34)NH$_2$; [Cha$^{24}$]hPTH(1–34) NH$_2$; [Nle$^{8, 18}$, Cha$^{27}$]hPTH(1–34)NH$_2$; [Cha$^{28}$]hPTH (1–34)NH$_2$; [Cha$^{31}$]hPTH(1–34)NH$_2$; [Cha$^{27}$]hPTH(1–34) NH$_2$; [Cha$^{27, 29}$]hPTH(1–34)NH$_2$; [Cha$^{28}$]bPTH(1–34) NH$_2$; [Cha$^{28}$]rPTH(1–34)NH$_2$; [Cha$^{24, 28, 31}$]hPTH(1–34) NH$_2$; [Aib$^{16}$]hPTH(1–34)NH$_2$; [Aib$^{19}$]hPTH(1–34)NH$_2$; [Aib$^{34}$]hPTH(1–34)NH$_2$; [Aib$^{16, 19}$]hPTH(1–34)NH$_2$; [Aib$^{16, 19, 34}$]bPTH(1–34)NH$_2$; [Aib$^{16, 34}$]hPTH(1–34)NH$_2$; [Aib$^{19, 34}$]hPTH(1–34)NH$_2$; [Cha$^{7, 11}$, Nle$^{8, 18}$, Aib$^{16, 19}$, Tyr$^{34}$]hPTH (1–34)NH$_2$; [Cha$^{7, 11}$, Nle$^{8, 18, 31}$, Aib$^{16, 19}$, Tyr$^{34}$]hPTH(1–34)NH$_2$; [Cha$^7$, Aib$^{16}$]hPTH(1–34)NH$_2$; [Cha$^{11}$, Aib$^{16}$]hPTH(1–34)$_2$; [Cha$^7$, Aib$^{34}$]hPTH(1–34) NH$_2$; [Cha$^{11}$, Aib$^{34}$]hPTH(1–34)NH$_2$; [Cha$^{27}$, Aib$^{16}$]hPTH (1–34)NH$_2$; [Cha$^{27}$, Aib$^{34}$]hPTH(1–34)NH$_2$; [Cha$^{28}$, Aib$^{16}$] hPTH(1–34)NH$_2$; [Cha$^{28}$, Aib$^{34}$]hPTH(1–34)NH$_2$; [Nle$^{31}$] hPTH (1–34)NH$_2$; [hArg$^{27}$]hPTH(1–34)NH$_2$; [Dap$^1$, Nle$^{8, 18}$, Tyr$^{34}$]hPTH (1–34)NH$_2$; [Nle$^{31}$]bPTH(1–34)NH$_2$; [Nle$^{31}$]rPTH (1–34)NH$_2$; [hArg$^{27}$]bPTH(1–34)NH$_2$; [hArg$^{27}$]rPTH(1–34)NH$_2$; [Cha$^{7, 11}$, Aib$^{19}$, Lys$^{30}$]hPTH (1–34)NH$_2$; [Aib$^{12}$]hPTH(1–34)NH$_2$; [Cha$^{24, 28, 31}$, Lys$^{30}$] hPTH(1–34)NH$_2$; [Cha$^{28, 31}$]hPTH(1–34)NH$_2$; [Cha$^{7, 11}$, Nle$^{8, 18}$, Aib$^{34}$]hPTH(1–34)NH$_2$; [Aib$^3$]hPTH(1–34)NH$_2$; [Cha$^8$]hPTH (1–34)NH$_2$; [Cha$^{15}$]hPTH(1–34)NH$_2$; [Cha$^{7, 11}$, Aib$^{19}$]hPTH(1–34)NH$_2$; [Cha$^{7, 11}$Aib$^{16}$]hPTH (1–34)NH$_2$; [Aib$^{17}$]hPTH(1–34)NH$_2$; [Cha]hPTH(1–34) NH$_2$;[Cha$^{7, 11, 15}$]hPTH(1–34)NH$_2$; [Cha$^{7, 11}$, Nle$^{8, 18}$, Aib$^{19}$, Tyr$^{34}$]hPTH(1–34)NH$_2$; [Cha$^{7, 11}$, Nle$^{8, 18}$, Aib$^{19}$, Lys$^{30}$, Tyr$^{34}$]hPTH(1–34)NH$_2$; [Cha$^{7, 11, 15}$]hPTH(1–34) NH$_2$; [Aib$^{17}$]hPTH(1–34)NH$_2$; [Cha$^{7, 11}$, Leu$^{27}$]hPTH (1–34)NH$_2$; [Cha$^{7, 11, 15}$, Leu$^{27}$]hPTH(1–34)NH$_2$; [Cha$^{7, 11, 27}$] hPTH(1–34)NH$_2$; [Cha$^{7, 11, 15, 27}$]hPTH (1–34)NH$_2$; [Trp$^{15}$]hPTH(1–34)NH$_2$; [Nal$^{15}$]hPTH (1–34)NH$_2$; [Trp$^{15}$, Cha$^{23}$]hPTH(1–34)NH$_2$; [Cha$^{15, 23}$]hPTH(1–34)NH$_2$; [Phe$^{7, 11}$]hPTH(1–34)NH$_2$; [Nal$^{7, 11}$]hPTH(1–34)NH$_2$; [Trp$^{7, 11}$]hPTH (1–34)NH$_2$; [Phe$^{7, 11, 15}$]hPTH(1–34)NH$_2$; [Nal$^{7, 11, 15}$]hPTH (1–34)NH$_2$; [Trp$^{7, 11, 15}$]hPTH(1–34)NH$_2$; and [Tyr$^{7, 11, 15}$]hPTH (1–34)NH$_2$.

In another aspect, this invention relates to peptides covered by the following formula:

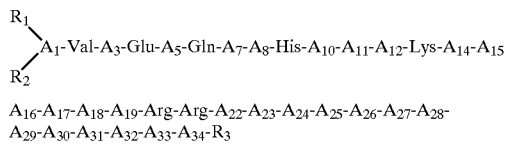

wherein
$A_1$ is Ala, Ser, or Dap;
$A_3$ is Ser or Aib;
$A_5$ is His, Ile, or Cha;
$A_7$ is Leu, Cha, Nle, β-Nal, Trp, Pal, Phe, or p-X-Phe in which X is OH, a halogen, or $CH_3$;
$A_8$ is Leu, Met, or Cha;
$A_{10}$ is Asp or Asn;
$A_{11}$ is Lys, Leu, Cha, Phe, or β-Nal;
$A_{12}$ is Gly or Aib;
$A_{14}$ is Ser or His;
$A_{15}$ is Ile, or Cha;
$A_{16}$ is Gln or Aib;
$A_{17}$ is Asp or Aib;
$A_{18}$ is Leu, Aib, or Cha;
$A_{19}$ is Arg or Aib;
$A_{22}$ is Phe, Glu, Aib, Acc, or Cha;
$A_{23}$ is Phe, Leu, Lys, Acc, or Cha;
$A_{24}$ is Leu, Lys, Acc, or Cha;
$A_{25}$ is His, Aib, or Glu;
$A_{26}$ is His, Aib, or Lys;
$A_{27}$ is Leu, Lys, Acc, or Cha;
$A_{28}$ is Ile, Leu, Lys, Acc, or Cha;
$A_{29}$ is Ala, Glu, or Aib;
$A_{30}$ is Glu, Cha, Aib, Acc, or Lys;
$A_{31}$ is Ile, Leu, Cha, Lys, Acc, or deleted;
$A_{32}$ is His or deleted;
$A_{33}$ is Thr or deleted;
$A_{34}$ is Ala or deleted;
each of $R_1$ and $R_2$ is, independently, H, $C_{1-12}$ alkanyl, $C_{7-20}$ phenylalkyl, $C_{11-20}$, naphthyalkyl, $C_{1-12}$, hydroxyalkyl, $C_{2-12}$ hydroxyalkenyl, $C_{7-20}$ hydroxyphenylalkyl, or $C_{11-20}$ hydroxynaphthylalkyl; or one and only one of $R_1$ and $R_2$ is $COE_1$ in which $E_1$ is $C_{1-12}$ alkyl, $C_{2-12}$ alkyl, $C_{2-12}$ alkenyl, $C_{7-20}$ phenylalkyl, $C_{11-20}$ naphthyalkyl, $C_{1-12}$ hydroxyalkyl, $C_{2-12}$ hydroxyalkenyl, $C_{7-20}$ hydroxyphenylalkyl, or $C_{11-20}$ hydroxynaphthylalkyl; and
$R_3$ is OH, $NH_2$, $C_{1-12}$ alkoxy, or NH—Y—$CH_2$—Z in which Y is a $C_{1-12}$ hydrocarbon moiety and Z is H, OH, $CO_2H$ or $CONH_2$;
provided that (i) at least one of $A_5$, $A_7$, $A_8$, $A_{11}$, $A_{15}$, $A_{18}$, $A_{22}$, $A_{23}$, $A_{24}$, $A_{27}$, $A_{28}$, $A_{30}$, or $A_{31}$ is Cha, or at least one of $A_3$, $A_{12}$, $A_{16}$, $A_{17}$, $A_{18}$, $Al_{19}$, $A_{22}$, $A_{25}$, $A_{26}$, $A_{29}$, $A_{30}$, or $A_{34}$ is Aib; or that (ii) at least one of $A_{23}$, $A_{24}$, $A_{27}$, $A_{28}$, or $A_{31}$ is Lys; or a pharmaceutically acceptable salt thereof. In one embodiment, at least one of $A_7$ and $A_{11}$ is Cha. In another embodiment, at least one of $A_{16}$ or $A_{19}$ is Aib. Specific examples of peptides of the just-recited formula include, but are not limited to, [Cha$^7$]hPTHrP(1–34)NH$_2$; [Cha$^{11}$]hPTHrP(1–34)NH$_2$; [Cha$^{7, 11}$]hPTHrP(1–34)NH$_2$; [Aib$^{16}$, Tyr$^{34}$]hPTHrP (1–34)NH$_2$; [Aib$^{19}$]hPTHrP(1–34)NH$_2$; [Aib$^{16, 19}$]hPTHrP(1–34)NH$_2$; [Cha$^{7, 11}$, Aib$^{16}$]hPTHrP (1–34)NH$_2$; [Cha$^{7, 11}$, Aib$^{19}$]hPTHrP(1–34)NH$_2$; [Cha$^{22}$, Leu$^{23, 28, 31}$, Glu$^{25, 29}$, LyS$^{26, 30}$]hPTHrP(1–34) NH$_2$; [Glu$^{22, 25, 29}$, Leu$^{23, 28, 31}$, Lys$^{26, 27, 30}$]hPTHrP (1–34)NH$_2$; [Cha$^{22, 23}$, Glu$^{25, 29}$ Leu$^{28, 31}$, Lys$^{26, 30}$]hPTHrP(1–34)NH$_2$; [Glu$^{22, 25}$, Leu$^{23, 28, 31}$, Aib$^{29}$, Lys$^{26, 30}$]hPTHrP(1–34)NH$_2$; [Glu$^{22, 25, 29}$, Lys$^{23, 26, 30}$, Leu$^{28, 31}$] hPTHrP (1–34)NH$_2$; [Glu$^{22, 25, 29}$, Leu$^{23, 28, 31}$, Lys$^{26}$, Cha$^{30}$] hPTHrP(1–34)NH$_2$; [Glu$^{22, 25, 29}$, Leu$^{23, 28, 31}$, Lys$^{26}$, Aib$^{30}$]hPTHrP(1–34)NH$_2$; [Glu$^{22, 25, 29}$, Leu$^{23, 31}$, Lys$^{26, 28, 30}$]hPTHrP(1–34)NH$_2$; [Cha$^{22, 23, 24, 27, 28, 31}$ Glu$^{25, 29}$, Lys$^{26, 30}$]hPTHrP(1–34)NH$_2$; [Glu$^{22, 25, 29}$, Cha$^{23, 24, 28, 31}$, Lys$^{26, 27, 30}$]hPTHrP(1–34)NH$_2$; [Glu$^{22, 25, 29}$, Cha$^{23, 24, 27, 31}$, Lys$^{26, 28, 30}$]hPTHrP (1–34)NH$_2$; [Glu$^{22, 25, 29}$, Lys$^{23, 26, 30}$, Cha$^{24, 27, 28, 31}$]hPTHrP(1–34)NH$_2$; [Cha$^{22}$, Leu$^{23, 28, 31}$, Glu$^{25, 29}$, Lys$^{26, 27, 30}$]hPTHrP(1–34)NH$_2$; [Cha$^{22}$, Leu$^{23, 31}$, Glu$^{25, 29}$, Lys$^{26, 28, 30}$]hPTHrP(1–34)NH$_2$; [Cha$^{22}$, Lys$^{23, 26, 30}$, Glu$^{25, 29}$, Leu$^{28, 31}$]hPTHrP(1–34)NH$_2$; [Cha$^{22}$, Leu$^{23, 28, 31}$, Glu$^{25}$, Lys$^{26, 30}$, Aib$^{29}$]hPTHrP(1–34)NH$_2$; [Cha$^{22}$, Leu$^{23, 28, 31}$, Glu$^{25, 29}$, Lys$^{26}$, Aib$^{30}$]hPTHrP (1–34)NH$_2$; [Glu$^{22, 25}$, Leu$^{23, 28, 31}$, Lys$^{26, 27, 30}$, Aib$^{29}$] hPTHrP(1–34)NH$_2$; [Glu$^{22, 25}$, Lys$^{23, 26, 30}$, Leu$^{28, 31}$, Aib$^{29}$]hPTHrP(1–34)NH$_2$; [Glu$^{22, 25}$, Leu$^{23, 31}$, Lys 26, 28, 30, Aib$^{29}$]hPTHrP(1–34)NH$_2$; [Cha$^{7, 11}$, Glu$^{22, 25, 29}$, Leu$^{23, 28, 31}$, Lys$^{26, 30}$]hPTHrP(1–34)NH$_2$; [Cha$^{7, 11, 22}$, Leu$^{23, 28, 31}$, Glu$^{25, 29}$, Lys$^{26, 30}$]hPTHrP (1–34)NH$_2$; [Cha$^{7, 11}$, Glu$^{22, 25, 29}$, Leu$^{23, 28, 31}$, Lys$^{26, 27, 30}$]hPTHrP(1–34)NH$_2$; [Cha$^{7, 11, 22, 23}$, Glu$^{25, 29}$, Leu$^{28, 31}$, Lys$^{26, 30}$]hPTHrP(1–34)NH$_2$; [Cha$^{7, 11}$, Glu$^{22, 25, 29}$, Lys$^{23, 26, 30}$, Leu$^{28, 31}$]hPTHrP (1–34)NH$_2$; [Cha$^{7, 11}$, Glu$^{22, 25, 29}$, Leu$^{23, 31}$, Lys$^{26, 28, 30}$]hPTHrP(1–34)NH$_2$; [Cha$^{7, 11}$, Glu$^{22, 25}$, Leu$^{23, 28, 31}$, Aib$^{29}$, Lys$^{26, 30}$]hPTHrP(1–34)NH$_2$; [Cha$^{7, 11}$, Glu$^{22, 25, 29}$, Leu$^{23, 28, 31}$, Lys$^{26}$, Aib$^{30}$]hPTHrP(1–34)NH$_2$; [Cha$^{15}$, Glu$^{22, 25, 29}$, Leu$^{23, 28, 31}$, Lys$^{26, 30}$]hPTHrP(1–34)NH$_2$; [Cha$^{15, 22}$, Leu$^{23, 28, 31}$, Glu$^{25, 29}$, Lys$^{26, 30}$]hPTHrP(1–34)NH$_2$; [Cha$^{15}$, Glu$^{22, 25, 29}$, Leu$^{23, 28, 31}$, Lys$^{26, 27, 30}$]hPTHrP(1–34)NH$_2$; [Cha$^{15, 22, 23}$, Glu$^{25, 29}$, Leu$^{28, 31}$, Lys$^{26, 30}$]hPTHrP(1–34)NH$_2$; [Cha$^{15}$, Glu$^{22, 25}$, Leu$^{23, 28, 31}$, Aib$^{29}$, Lys$^{26, 30}$]hPTHrP(1–34)NH$_2$; [Cha$^{15}$, Glu$^{22, 25, 29}$, Lys$^{23, 26, 30}$, Leu$^{28, 31}$]hPTHrP(1–34)NH$_2$; [Cha$^{15}$, Glu$^{22, 25, 29}$, Leu$^{23, 28, 31}$, Lys$^{26, Aib30}$]hPTHrP(1–34)NH$_2$; [Cha$^{15}$, Glu$^{22, 28, 29}$, Leu$^{23, 31}$, Lys$^{26, 28, 30}$]hPTHrP(1–34)NH$_2$; [Cha$^{15, 30}$, Glu$^{22, 25, 29}$, Leu$^{23, 28, 31}$, Lys$^{26}$]hPTHrP(1–34)NH$_2$; [Cha$^{7, 8, 22}$, Leu$^{23, 28, 31}$, Glu$^{25, 29}$, Lys$^{26, 30}$]hPTHrP (1–34)NH$_2$; [Cha$^{7, 8}$, Glu$^{22, 25, 29}$, Leu$^{23, 28, 31}$, Lys$^{26, 27, 30}$]hPTHrP(1–34)NH$_2$; [Cha$^{7, 8, 22, 23}$, Glu$^{25, 29}$, Leu$^{28, 31}$, Lys$^{26, 30}$]hPTHrP (1–34)NH$_2$; [Cha$^{7, 8}$, Glu$^{22, 25, 29}$, Leu$^{23, 28, 31}$, Lys$^{26, 30}$]hPTHrP(1–34)NH$_2$; [Cha$^{7, 8}$, Glu$^{22, 25}$, Leu$^{23, 28, 31}$, Aib$^{29}$, Lys$^{26, 30}$]hPTHrP (1–34)NH$_2$; [Cha$^{7, 8}$, Glu$^{22, 25, 29}$, Lys$^{23, 26, 30}$, Leu$^{28, 31}$]hPTHrP(1–34)NH$_2$; [Cha$^{7, 8}$, Glu$^{22, 25, 29}$, Leu$^{23, 28, 31}$, Lys$^{26}$, Aib$^{30}$] hPTHrP(1–34)NH$_2$; [Cha$^{7, 8}$, Glu$^{22, 25, 29}$, Leu$^{23, 31}$, Lys$^{26, 28, 30}$]hPTHrP(1–34)NH$_2$; [Cha$^{7, 8, 30}$, Glu$^{22, 25, 29}$, Leu$^{23, 28, 31}$, Lys$^{26}$]hPTHrP(1–34)NH$_2$; [Ser$^1$, Ile$^5$, Cha$^{7, 11, 22}$, Met$^8$, Asn$_{10}$, His$^{14}$, Leu$^{23, 28, 31}$, Glu$^{25, 29}$, Lys$^{26, 30}$]hPTHrP (1–34)NH$_2$; [Ser$^1$, Ile$^5$, Cha$^{7, 11}$, Met$^8$, Asn$^{10}$, His$^{14}$, Glu$^{22, 25, 29}$, Leu$^{23, 28, 31}$, Lys$^{26, 27, 30}$]hPTHrP(1–34)NH$_2$; [Ser$^1$, Ile$^5$, Cha$^{7, 11}$, Met$^8$, Asn$^{10}$, His$^{14}$, Glu$^{22, 25, 29}$, Leu$^{23, 31}$, Lys$^{26, 28, 30}$]hPTHrP(1–34)NH$_2$; Ser$^1$, Ile$^5$, Cha$^{7, 11}$, Met$^8$, Asn$^{10}$, His$^{14}$, Glu$^{22, 25, 29}$, Lys$^{23, 26, 30}$, Leu$^{28, 31}$]hPTHrP(1–34)NH$_2$; [Ser$^1$, Ile$^5$, Cha$^{7, 11}$, Met$^8$, Asn$^{10}$, His$^{14}$, Glu$^{22, 25}$, Leu$^{23, 28, 31}$, Aib$^{29}$, Lys$^{26, 30}$]hPTHrP(1–34)NH$_2$; [Ser$^1$, Ile$^5$, Cha$^{7, 11}$, Met$^8$, Asn$^{10}$, His$^{14}$, Glu$^{22, 25, 29}$, Leu$^{23, 28, 31}$, Lys$^{26}$, Aib$^{30}$] PTHrP(1–34)NH$_2$; [Ser$^1$, Ile$^5$, Cha$^{7, 11, 22, 23}$, Met$^8$, Asn$^{10}$, His$^{14}$, Glu$^{25, 29}$, Leu$^{28, 31}$, Lys$^{26, 30}$]hPTHrP(1–34) NH$_2$; [Ser$^1$, Ile$^5$, Cha$^{7, 11, 15, Met8}$, Asn$^{10}$, His$^{14}$]hPTHrP(1–34)NH$_2$; [Ser$^1$, Ile$^5$, Met$^8$, Asn$^{10}$, Leu$^{11, 28, 31}$, His$^{14}$, Aib$^{16}$]hPTHrP (1–34)NH$_2$; [Ser$^1$, Ile$^5$, Met$^8$, Asn$^{10}$, Leu$^{11, 28, 31}$, His$^{14}$, Cha$^{22, 23}$, Glu$^{25, 29}$, Lys$^{26, 30}$]hPTHrP (1–34)NH$_2$; [Ser$^1$, Ile$^5$, Cha$^{7, 11}$, Met$^8$, Asn$^{10}$, His$^{14}$, Glu$^{22, 25, 29}$, Leu$^{23, 28, 31}$, Lys$^{26, 30}$]hPTHrP(1–34)NH$_2$; [Ser$^1$, Ile$^{5, 7}$, Met$^8$, Asn$^{210}$, His$^{14}$, Cha$^{15}$, Glu$^{22, 25, 29}$, Leu$^{23, 28, 31}$, Lys$^{26, 30}$]hPTHrP (1–34)NH$_2$; [Ser$^1$, Ile$^5$, Cha$^{7, 8}$, Asn$^{10}$, His$^{14}$, Glu$^{22, 25, 29}$, Leu$^{23, 28, 31}$, Lys$^{26, 30}$]hPTHrP(1–34)NH$_2$; [Glu$^{22, 25, 29}$, Leu$^{23, 28, 31}$, Lys$^{24, 26, 30}$]hPTHrP(1–34)NH$_2$; [Aib$^{22}$, Leu$^{23, 28, 31}$, Glu$^{25, 29}$, Lys$^{26, 30}$]hPTHrP(1–34)NH$_2$; [Glu$^{22, 29}$, Leu$^{23, 28, 31}$, Aib$^{25}$, Lys$^{26, 30}$]hPTHrP (1–34)NH$_2$; [Glu$^{22, 25, 29}$, Leu$^{23, 28, 31}$, Aib$^{26}$, Lys$^{30}$]hPTHrP(1–34) NH$_2$; [Glu$^{22, 25, 29}$, Leu$^{23, 28}$, Lys$^{26, 30, 31}$] hPTHrP (1–34)NH$_2$; [Ser$^1$, Ile$^5$, Met$^8$, Asn$^{10}$, Leu$^{11, 23, 28, 31}$, His$^{14}$, Cha$^{22}$, Glu$^{25, 29}$, Lys$^{26, 30}$] hPTHrP(1–34)NH$_2$; [Ser$^1$, Ile$^5$, Met$^8$, Asn$^{10}$, Leu$^{11, 28, 31}$, His$^{14}$, Glu$^{22, 25, 29}$, Lys$^{23, 26, 30}$]PTHrP(1–34)NH$_2$; [Ser$^1$, Ile$^5$, Met$^8$, Asn$^{10}$, Leu$^{11, 23, 28, 31}$, His$^{14}$, Glu$^{22, 25, 29}$, Lys$^{26, 27, 30}$] hPTHrP (1–34)NH$_2$; [Ser$^1$, Ile$^5$, Met$^8$, Asn$^{10}$, Leu$^{11, 23, 31}$, His$^{14}$, Glu$^{22, 25, 29}$, Lys$^{26, 28, 30}$] hPTHrP(1–34)NH$_2$; [Ser$^1$, Ile$^5$, Met$^8$, Asn$^{10}$, Leu$^{11, 23, 28, 31}$, His$^{14}$, Glu$^{22, 25}$, Aib$^{29}$, Lys$^{26, 30}$] hPTHrP (1–34)NH$_2$; [Ser$^1$, Ile$^5$, Met$^8$, Asn$^{10}$, Leu$^{11, 23, 28, 31}$, His$^{14}$, Glu$^{22, 25, 29}$, Lys$^{26}$, Aib$^{30}$]hPTHrP(1–34)NH$_2$; or [Ser$^1$, Ile$^5$, Met$^8$] hPTHrP(1–34)NH$_2$; [Glu$^{22, 25}$, Ahc$^{23}$, Lys$^{26, 30}$, Leu$^{28, 31}$, Aib$^{29}$]hPTHrP(1–34)NH$_2$; [Glu$^{22, 25}$, Leu$^{23, 28, 31}$, Lys$^{26, 30}$, Ahc$^{27}$, Aib$^{29}$]hPTHrP(1–34)NH$_2$; [Glu$^{22, 25}$, Leu$^{23, 28}$, Lys$^{26, 30}$, Aib$^{29}$, Ahc$^{31}$]hPTHrP(1–34)NH$_2$; [Glu$^{22, 25}$, Cha$^{23}$, Lys$^{26, 30}$, Leu$^{28, 31}$, Aib$^{29}$]hPTHrP (1–34)NH$_2$; [Glu$^{22, 25}$, Cha$^{23}$, Lys$^{26, 30}$, Leu$^{28}$, Aib$^{29}$]hPTHrP(1–34)NH$_2$; [Glu$^{22, 25}$, Cha$^{23}$, Lys$^{26, 30}$, Aib$^{29}$]hPTHrP (1–34)NH$_2$; [Ahc$^{22}$, Leu$^{23, 28, 31}$, Glu$^{25}$, Lys$^{26, 30}$, Aib$^{29}$]hPTHrP(1–34)NH$_2$; [Glu$^{22, 25}$, Leu$^{23, 28, 31}$, Lys$^{26}$, Aib$^{29}$, Ahc$^{30}$]hPTHrP(1–34)NH$_2$; [Glu$^{22, 25}$, Cha$^{23}$, Lys$^{26, 30}$, Aib$^{29}$, Leu$^{31}$]hPTHrP(1–34) NH$_2$; [Glu$^{22, 25}$, Leu$^{23, 28, 31}$, Ahc$^{24}$, Lys$^{26, 30}$, Aib$^{29}$]hPTHrP(1–34)NH$_2$; [Glu$^{22, 25}$, Leu$^{23, 31}$, Lys$^{26, 30}$, Ahc$^{28}$, Aib$^{29}$]hPTHrP(1–34)NH$_2$; [Glu$^{22, 25}$, Leu$^{23, 28, 31}$, Lys$^{26, Aib29, 30}$]hPTHrP(1–34)NH$_2$; [Aib$^{22, 29}$, Leu$^{23, 28, 31}$, Glu$^{25}$, Lys$^{26, 30}$]hPTHrP(1–34)NH$_2$; [Glu$^{22, 25}$, Leu$^{23, 28, 31}$, Aib$^{26, 29}$, Lys$^{30}$]hPTHrP(1–34) NH$_2$; [Cha$^{22}$, Ahc$^{23}$, Glu$^{25, 29}$, Lys$^{26, 30}$, Leu$^{28, 31}$]hPTHrP(1–34)NH$_2$; [Cha$^{22}$, Leu$^{23, 28, 31}$, Ahc$^{24}$, Glu$^{25, 29}$, Lys$^{26, 30}$]hPTHrP(1–34)NH$_2$; [Cha$^{22}$, Leu$^{23, 28, 31}$, Glu$^{25, 29}$, Lys$^{26, 30}$, Ahc$^{27}$]hPTHrP(1–34) NH$_2$; [Cha$^{22}$, Leu$^{23, 31}$, Glu$^{25, 29}$, Lys$^{26, 30}$, Ahc$^{28}$]hPTHrP(1–34)NH$_2$; [Cha$^{22}$, Leu$^{23, 28, 31}$, Glu$^{25, 29}$, Lys$^{26}$, Leu$^{28}$, Ahc$^{30}$]hPTHrP(1–34)NH$_2$; [Cha$^{22, 23}$, Glu$^{25, 29}$, Lys$^{26, 30}$, Leu$^{31}$]hPTHrP (1–34)NH$_2$; [Cha$^{22}$, Leu$^{23, 28}$, Glu$^{25, 29}$, Lys$^{26, 30}$, Ahc$^{31}$]hPTHrP (1–34)NH$_2$; [Cha$^{22, 23}$, Glu$^{25, 29}$, Lys$^{26, 30}$, Leu$^{31}$]hPTHrP(1–34) NH$_2$; [Cha$^{22, 23}$, Glu$^{25, 29}$, Lys$^{26, 30}$, Leu$^{28}$]hPTHrP (1–34)NH$_2$; [Cha$^{22, 23}$, Glu$^{25, 29}$, Lys$^{26, 30}$] hPTHrP (1–34)NH$_2$; [Glu$^{22}$, Leu$^{23, 28, 31}$, Aib$^{25, 29}$, Lys$^{26, 30}$]hPTHrP(1–34)NH$_2$; [Glu$^{22, 29}$, Ahc$^{23}$, Aib$^{25}$, Lys$^{26, 30}$, Leu$^{28, 31}$]hPTHrP(1–34)NH$_2$; [Ahc$^{22}$, Leu$^{23, 28, 31}$, Aib$^{25}$, Lys$^{26, 30}$, Glu$^{29}$] hPTHrP(1–34) NH$_2$; [Aib$^{22, 25}$, Leu$^{23, 28, 31}$, Lys$^{26, 30}$, Glu$^{29}$]hPTHrP(1–34)NH$_2$; [Glu$^{22, 29}$, Leu$^{23, 28, 31}$, Ahc$^{24}$, Aib$^{25}$, Lys$^{26, 30}$]hPTHrP(1–34)NH$_2$; [Glu$^{22, 29}$, Leu$^{23, 28, 31}$, Aib$^{25, 26, Lys30}$]hPTHrP(1–34)NH$_2$; [Glu$^{22, 29}$, Leu$^{23, 28, 31}$, Aib$^{25}$, Lys$^{26, 30}$, Ahc$^{27}$] hPTHrP(1–34) NH$_2$; [Glu$^{22, 29}$, Leu$^{23, 31}$, Aib$^{25}$, Lys$^{26, 30, Ahc28}$]hPTHrP(1–34)NH$_2$; [Glu$^{22, 29}$, Leu$^{23, 28}$, Aib$^{25}$, Lys$^{26, 30}$, Ahc$^{31}$]hPTHrP(1–34)NH$_2$; [Glu$^{22, 29}$, Leu$^{23, 28, 31}$, Aib$^{25, 30}$, Lys$^{26}$]hPTHrP(1–34)NH$_2$; [Glu$^{22, 29}$, Leu$^{23, 28, 31}$, Aib$^{25}$, Lys$^{26}$, Ahc$^{30}$]hPTHrP(1–34)NH$_2$; [Glu$^{22, 29}$, Cha$^{23}$, Aib$^{25}$, Lys$^{26, 30}$, Leu$^{28, 31}$]hPTHrP (1–34))NH$_2$; [Glu$^{22, 29}$, Cha$^{23}$, Aib$^{25}$, Lys$^{26, 30}$, Leu$^{28, 31}$]hPTHrP(1–34)NH$_2$; [Glu$^{22, 29}$, Cha$^{23}$, Aib$^{25}$, Lys$^{26, 30}$]hPTHrP(1–34)NH$_2$; [Glu$^{22, 29}$, Cha$^{23}$, Aib$^{25}$, Lys$^{26, 30}$, Leu$^{28}$]hPTHrP(1–34)NH$_2$; [Glu$^{22, 25, 29}$, Cha$^{23}$, Lys$^{26}$, Leu$^{28, 31}$, Aib$^{30}$] hPTHrP (1–34)NH$_2$; [Glu$^{22, 25, 29}$, Cha$^{23}$, Lys$^{26, Aib30}$, Leu$^{31}$]hPTHrP(1–34) NH$_2$; [Glu$^{22, 25, 29}$, Cha$^{23}$, Lys$^{26}$, Aib$^{30}$]hPTHrP(1–34) NH$_2$; [Glu$^{22, 25, 29}$, Cha$^{23}$Lys$^{26}$, Leu$^{28}$, Aib$^{30}$]hPTHrP (1–34)NH$_2$; [Glu$^{22, 25, 29}$, Leu$^{23, 28, 31}$, Lys$^{26, Ahc27}$, Aib$^{30}$] hPTHrP(1–34)NH$_2$; [Glu$^{22, 25, 29}$, Leu$^{23, 28, 31}$, Ahc$^{24}$, Lys$^{26}$, Aib$^{30}$]hPTHrP(1–34)NH$_2$; [Ahc$^{22}$, Leu$^{23}$, $_{28, 31}$, Glu$^{25, 29}$, Lys$^{26}$, Aib$^{30}$]hPTHrP(1–34)NH$_2$; [Aib$^{22, 30}$, Leu$^{23, 28, 31}$, Glu$^{25, 29}$, Lys$^{26}$]hPTHrP(1–34)NH$_2$; [Glu$^{22, 25}$, Leu$^{23, 28}$, Lys$^{26, 30, 31}$, Aib$^{29}$]hPTHrP (1–34) NH$_2$; [Cha$^{22}$, Leu$^{23, 28}$, Glu$^{25, 29}$, Lys$^{26, 30, 31}$]hPTHrP (1–34)NH$_2$; [Ahc$^{22}$, Leu$^{23, 28}$, Glu$^{25, 29}$, Lys$^{26, 30, 31}$] hPTHrP(1–34)NH$_2$; [Glu$^{22, 25, 29}$, Leu$^{23, 28}$, Lys$^{26, 30, 31}$, Ahc$^{30}$]hPTHrP (1–34)NH$_2$; [Glu$^{22, 25, 29}$, Leu$_{23, 28, 31}$, Lys$^{26}$, Ahc$^{30}$]hPTHrP(1–34)NH$_2$; [Ahc$^{22}$, Leu$_{23, 28, 31}$, Glu$^{25, 29}$, Lys$^{26, 30}$]hPTHrP (1–34)NH$_2$; [Glu$^{22, 25, 29}$, Leu$^{23, 28}$, Lys$^{26, 30, 31}$, Ahc$^{27}$]hPTHrP (1–34)NH$_2$.

With the exception of the N-terminal amino acid, all abbreviations (e.g. Ala or A$_1$) of amino acids in this disclosure stand for the structure of —NH—CH(R)—CO—, wherein R is a side chain of an amino acid (e.g., CH$_3$ for Ala). For the N-terminal amino acid, the abbreviation stands for the structure of =N—CH(R)—CO—, wherein R is a side chain of an amino acid. β-Nal, Nle, Dap, Cha, Nva, Amp, Pal, Ahc, and Aib are the abbreviations of the following α-amino acids: β-(2-naphthyl)alanine, norleucine, α,β-diaminopropionic acid, cyclohexylalanine, norvaline, 4-amino-phenylalanine, 3-pyridinylalanine, α-aminocyclohexanecarboxylic acid, and α-aminoisobutyric acid, respectively. What is meant by Acc is an amino acid selected from the group of α-aminopropanecarboxylic acid; α-aminobutanecarboxylic acid; α-aminopentanecarboxylic acid; α-aminohexanecarboxylic acid; α-aminoheptanecarboxylic acid; α-aminooctanecarboxylic acid; and α-aminononanecarboxylic acid. In the above formula, hydroxyalkyl, hydroxyphenyl-alkyl, and hydroxynaphthylalkyl may contain 1–4, hydroxy substituents. Also, COE$_1$ stands for —C=O·E$_1$. Examples of —C=O·E$_1$ include, but are not limited to, acetyl and phenylpropionyl.

A peptide of this invention is also denoted herein by another format, e.g., [Cha$^{7, 11}$]hPTH(1–34)NH$_2$, with the substituted amino acids from the natural sequence placed between the second set of brackets (e.g., Cha$^7$ for Leu$^7$, and Cha$^{11}$ for Leu$^{11}$ in hPTH). The abbreviation hPTH stands for human PTH, hPTHrP for human PTHrP, rPTH for rat PTH, and bPTH for bovine PTH. The numbers between the parentheses refer to the number of amino acids present in the peptide (e.g., hPTH(1–34) is amino acids 1, through 34 of the peptide sequence for human PTH). The sequences for hPTH(1–34), hPTHrP(1–34), bPTH(1–34), and rPTH(1–34) are listed in Nissenson, et al., Receptor, 3:193 (1993). The designation "NH$_2$" in PTH(1–34)NH$_2$ indicates that the C-terminus of the peptide is amidated. PTH(1–34), on the other hand, has a free acid C-terminus.

Each of the peptides of the invention is capable of stimulating the growth of bone in a subject (i.e., a mammal such as a human patient). Thus, it is useful in the treatment of osteoporosis and bone fractures when administered alone or concurrently with antiresorptive therapy, e.g., bisphosphonates and calcitonin.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

A therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, or by intratracheally) to a subject. The pill, tablet, or capsule that is to be administered orally can be coated with a substance for protecting the active composition from the gastric acid or intestinal enzymes in the stomach for a period of time sufficient to allow it to pass undigested into the small intestine. The therapeutic composition can also be in the form of a biodegradable or nonbiodegradable sustained release formulation for subcutaneous or intramuscular administration. See, e.g., U.S. Pat. No. 3,773,919 and 4,767, 628 and PCT Application No. WO 94/15587. Continuous administration can also be achieved using an implantable or external pump (e.g., INFUSAID™ pump). The administration can also be conducted intermittently, e.g., single daily injection, or continuously at a low dose, e.g., sustained release formulation.

The dose of a peptide of the present invention for treating the above-mentioned diseases or disorders varies depending upon the manner of administration, the age and the body weight of the subject, and the condition of the subject to be treated, and ultimately will be decided by the attending physician or veterinarian.

Also contemplated within the scope of this invention is a peptide covered by the above generic formula for use in treating diseases or disorders associated with deficiency in bone growth or the like, e.g., osteoporosis or fractures.

Other features and advantages of the present invention will be apparent from the detailed description and from the claims.

DETAILED DESCRIPTION OF THE INVENTION

Based on the description herein, the present invention can be utilized to its fullest extent. The following specific examples are to be construed as merely illustrative, and not limitative of the remainder of the disclosure in any way whatsoever. Further, all publications cited herein are incorporated by reference.

Structure

PTH(1–34) has been reported to have two amphophilic alpha helical domains. See, e.g., Barden, et al., Biochem., 32:7126 (1992). The first α-helix is formed between amino acid residues 4 through 13, while the second α-helix is formed between amino acid residues 21 through 29. Some peptides of this invention contain the substitution of Cha for one or more residues within or near these two regions of PTH(1–34), e.g., Cha$^7$ and Cha$^{11}$ within the first α-helix or Cha$^{27}$ and Cha$^{28}$ within the second α-helix.

Also covered by this invention are variants of PTH(1–34) with the substitution of Aib for a residue adjacent to the α-helixes, e.g., Aib$^{16}$, Aib$^{19}$, and Aib$^{34}$; hArg$^{27}$ and Nle$^{31}$, or the substitution of Dpa for the N-terminal residue.

Synthesis

The peptides of the invention can be prepared by standard solid phase synthesis. See, e.g., Stewart, J. M., et al., Solid Phase Synthesis (Pierce Chemical Co., 2d ed. 1984). The following is a description of how [Aib$^{34}$]hPTH (1–34)NH$_2$ was prepared. Other peptides of the invention can be prepared in an analogous manner by a person of ordinary skill in the art.

The peptide was synthesized on an Applied Biosystems (Foster City, Calif.) model 430A peptide synthesizer which was modified to do accelerated Boc-chemistry solid phase peptide synthesis. See Schnoize, et al., Int. J. Peptide Protein Res., 90:180 (1992). 4-Methylbenz-hydrylamine (MBHA) resin (Peninsula, Belmont, Calif.) with the substitution of 0.93 mmol/g was used. The Boc amino acids (Bachem, Calif., Torrance, Calif.; Nova Biochem., Lajolla, Calif.) were used with the following side chain protection: Boc-Arg(Tos)—OH, Boc-Asp(OcHxl)—OH, Boc-Asn(Xan)—OH, Boc-Glu(OcHxl)—OH, Boc-His(DNP)—OH, Boc-Asn-GH, Boc-Val-OH, Boc-Leu-OH, Boc-Ser-OH, Boc-Gly-OH, Boc-Met-OH, Boc-Gln-OH, Boc-Ile-OH, Boc-Lys(2ClZ)—OH, Boc-Ser(Bzl)—OH, and Boc-Trp(Fm)—OH. The synthesis was carried out on a 0.14 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min except for the Boc-Aib-OH and the following residue, Boc-Asn(Xan)—OH, wherein the coupling times were 20 min.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. After neutralization of the peptide-resin with 10% DIEA in DMF (1×1 min.), the formyl group on the side chain of Trp was removed by treatment with a solution of 15% ethanolamine/15% water/70% DMF for 2×30 min. The partially-deprotected peptide-resin was washed with DMF and DCM and dried under reduced pressure. The final cleavage was done by stirring the peptide-resin in 10 mL of HF containing 1 mL of anisole at 0°C. for 75 min. HF was removed by a flow of nitrogen. The residue was washed with ether (6×10 mL) and extracted with 4N HOAc (6×10 mL).

The peptide mixture in the aqueous extract was purified on a reversed-phase preparative high pressure liquid chromatography (HPLC) using a reversed phase VYDAC $C_{18}$ column (Nest Group, Southborough, Mass.). The column was eluted with a linear gradient (10% to 45% of solution B over 130 min.) at a flow rate of 10 mL/min (Solution A=0.1% aqueous TFA; Solution B=acetonitile containing 0.1% of TFA). Fractions were collected and checked on analytical HPLC. Those containing pure product were combined and lyophilized to dryness. 62.3 mg of a white solid was obtained. Purity was >99% based on analytical HPLC analysis. Electro-spray mass spectrometer analysis gave the molecular weight at 4054.7 (in agreement with the calculated molecular weight of 4054.7).

The synthesis and purification of [$Cha^{7, 11}$]hPTH (1–34)$NH_2$ was carried out in the same manner as the above synthesis of [$Aib^{34}$]hPTH(1–34)$NH_2$. The protected amino acid Boc-Cha-OH was purchased from Bachem, Calif. The purity of the final product was >98%, and the electron-spray mass spectrometer gave the molecular weight at 4197.0 (calculated molecular weight is 4196.9).

The full names for the abbreviations used above are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2ClZ for 2-chlorobenzyloxycarbonyl and OcHxl for O-cyclohexyl.

The substituents $R_1$ and $R_2$ of the above generic formula may be attached to the free amine of the N-terminal amino acid by standard methods known in the art. For example, alkyl groups, e.g., $C_{1-12}$ alkyl, may be attached using reductive alkylation. Hydroxyalkyl groups, e.g., $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amine of the N-terminal amino acid by mixing the completed resin with 3 molar equivalents of both the free acid and diisopropylcarbodiimide in methylene chloride for one hour and cycling the resulting resin through steps (a) to (f) in the above wash program. If the free acid contains a free hydroxy group, e.g., p-hydroxyphenylpropionic acid, then the coupling should be performed with an additional 3 molar equivalents of HOBT.

Other peptides of this invention can be prepared in an analogous manner by a person of ordinary skill in the art.

Functional Assays

A. Binding to PTH Receptor

The peptides of the invention were tested for their ability to bind to the PTH receptor present on SaOS-2 (human osteosarcoma cells). SaOS-2 cells (American Type Culture Collection, Rockville, Md.; ATCC #HTB 85) were maintained in RPMI 1640 medium (Sigma, St. Louis, Mo.) supplemented with 10% fetal bovine serum (FBS) and 2 mM glutamine at 37° C. in a humidified atmosphere of 5% $CO_2$ in air. The medium was changed every three or four days, and the cells were subcultured every week by trypsinization.

SaOS-2 cells were maintained for four days until they had reached confluence. The medium was replaced with 5% FBS in RPMI 1640 medium and incubated for 2 hrs at room temperature with $10×10^4$ cpm mono-$^{125}$I-[$Nle^{8,18}$, $Tyr^{34}$(3-$^{125}$I)]bPTH(1–34)$NH_2$ in the presence of a competing peptides of the invention at various concentrations between $10^{-11}$M to $10^{-4}$ M. The cells were washed four times with ice-cold PBS and lysed with 0.1 M NaOH, and the radioactivity associated with the cells was counted in a scintillation counter. Synthesis of mono-$^{125}$I-[$Nle^{8,18}$, $Tyr^{34}$(3-$^{125}$I)] bPTH(1–34)$NH_2$ was carried out as described in Goldman, M. E., et al., Endocrinol., 123:1468 (1988).

The binding assay was conducted with various peptides of the invention, and the $IC_{50}$ value, (half maximal inhibition of binding of mono-$^{125}$I-[$Nle^{8,18}$, $Tyr^{34}$(3-$^{125}$I)]bPTH(1–34)$NH_2$, for each peptide was calculated.

As shown in Table I, all of the tested peptides had a high binding affinity for the PTH receptor on the SaOS-2 cell.

B. Stimulation of Adenylate Cyclase Activity

The ability of the peptides of the invention to induce a biological response in SaOS-2 cells were measured. More specifically, any stimulation of the adenylate cyclase was determined by measuring the level of synthesis of cAMP (adenosine 3', 5'-monophosphate) as described previously in Rodan, et al., J. Clin. Invest. 72: 1511 (1983) and Goldman, et al., Endocrinol., 123:1468 (1988). Confluent SAOS-2 cells in 24 wells plates were incubated with 0.5 $\mu$Ci [$^3$H] adenine (26.9 Ci/mmol, New England Nuclear, Boston, Mass.) in fresh medium at 37° C. for 2 hrs, and washed twice with Hank's balanced salt solution (Gibco, Gaithersburg, Md.). The cells were treated with 1 mM IBMX [isobutylmethyl-xanthine, Sigma, St. Louis, Mo.] in fresh medium for 15 min, and the peptides of the invention were added to the medium to incubate for 5 min. The reaction was stopped by the addition of 1.2 M trichloroacetic acid (TCA) (Sigma, St. Louis, Mo.) followed by sample neutralization with 4 N KOH. cAMP was isolated by the two-column chromatographic method (Salmon, et al., 1974, Anal. Biochem. 58, 541). The radioactivity was counted in a scintillation counter (Liquid Scintillation Counter 2200CA, PACKARD, Downers Grove, Ill.).

The respective $EC_{50}$ values (half maximal stimulation of adenylate cyclase) for the tested peptides were calculated and shown in Table I. All tested peptides were found to be potent stimulators of adenylate cyclase activity, which is a biochemical pathway indicative as a proximal signal for osteoblast proliferation (e.g., bone growth).

TABLE I

| PEPTIDE | Kd ($\mu$M) | $EC_{50}$ (nM) |
|---|---|---|
| [Cha$^{7,11}$]hPTH(1–34)NH$_2$ | 0.01 | 0.6 |
| [Cha$^{23}$]hPTH(1–34)NH$_2$ | 0.2 | 20 |
| [Cha$^{24}$]hPTH(1–34)NH$_2$ | 0.1 | 10 |
| [Nle$^{8,18}$,Cba$^{27}$]hPTH(1–34)NH$_2$; | 0.05 | 2 |
| [Cha$^{28}$]hPTH(1–34)NH$_2$ | 0.05 | 2.5 |
| [Cha$^{31}$]hPTH(1–34)NH$_2$ | 0.03 | 4 |
| [Aib$^{16}$]hPTH(1–34)NH$_2$; | 0.004 | 0.7 |
| [Aib$^{19}$]hPTH(1–34)NH$_2$; | 0.005 | 0.6 |
| [Aib$^{34}$]hPTH(1–34)NH$_2$; | 0.007 | 3 |
| [Nle$^{31}$]hPTH(1–34)NH$_2$; | 0.004 | 0.7 |
| [hArg$^{27}$]hPTH(1–34)NH$_2$ | 0.007 | 1 |
| [Dap, Nle$^{8,18}$,Tyr$^{34}$]hPTH(1–34)NH$_2$ | 0.150 | 10 |
| [Cha$^{24,28,31}$,Lys$^{30}$]bPTH(1–34)NH$_2$; | 0.5 | 7 |
| [Cha$^{7,11}$,Nle$^{8,18}$,Tyr$^{34}$]hPTH(1–34)NH$_2$ | 0.006 | 0.6 |
| [Cha$^{7,11}$,Nle$^{8,18}$,Aib$^{16,19}$,Tyr$^{34}$]hPTH(1–34)NH$_2$ | 0.005 | 1.5 |
| [Cha$^{7,11}$,Nle$^{8,18,31}$, Aib$^{16,19}$,Tyr$^{34}$]hPTH(1–34)NH$_2$ | 0.04 | 4 |
| [Cha$^{11}$]hPTH(1–34)NH$_2$ | 0.005 | 2 |
| [Cha$^{28,31}$]hPTH(1–34)NH$_2$ | 0.06 | 7 |

TABLE I-continued

| PEPTIDE | Kd ($\mu$M) | $EC_{50}$ (nM) |
|---|---|---|
| [Cha$^{7,11}$,Nle$^{8,18}$,Aib$^{34}$]hPTH(1–34)NH$_2$ | 0.03 | 1.5 |
| [Cha$^{15}$]hPTH(1–34)NH$_2$ | 0.005 | 1.3 |
| [Cha$^{7,11}$,Aib$^{19}$]hPTH(1–34)NH$_2$ | 0.007 | 0.5 |
| [Cha$^{7,11}$,Aib$^{16}$]hPTH(1–34)NH$_2$ | 0.004 | 1.1 |
| [Aib$^{16,19}$]hPTH(1–34)NH$_2$ | 0.004 | 0.6 |
| [Aib$^{12}$]hPTH(1–34)NH$_2$ | 0.005 | 2 |
| [Aib$^3$]hPTH(1–34)NH$_2$ | 0.004 | 1.1 |
| [Cha$^{7,11}$,Aib$^{19}$,Lys$^{30}$]hPTH(1–34)NH$_2$ | 0.004 | 2 |
| [Cha$^7$]hPTH(1–34)NH$_2$ | 0.02 | 2.3 |
| [Cha$^{24,28,31}$]hPTH(1–34)NH$_2$ | 1.0 | 30 |
| [Aib$^{17}$]hPTH(1–34) | 0.05 | 3 |
| [Cha$^{7,11,15}$]hPTH(1–34) | 0.01 | 1.4 |

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. The compound of the formula [Glu$^{22,25}$, Leu$^{23,28,31}$, Aib$^{29}$, Lys$^{26,30}$]hPTHrP(1–34)NH$_2$.

* * * * *